US012678551B2

(12) United States Patent
Wiener

(10) Patent No.: US 12,678,551 B2
(45) Date of Patent: Jul. 14, 2026

(54) PORTABLE SUCTION DEVICES, SYSTEMS, AND METHODS FOR CONTROLLING SUCTION USING SAME

(71) Applicant: The Research Foundation for the State University of New York, Albany, NY (US)

(72) Inventor: Scott Wiener, Camillus, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 1150 days.

(21) Appl. No.: 17/682,855

(22) Filed: Feb. 28, 2022

(65) Prior Publication Data

US 2022/0273860 A1 Sep. 1, 2022

Related U.S. Application Data

(60) Provisional application No. 63/154,024, filed on Feb. 26, 2021.

(51) Int. Cl.
*A61M 1/00* (2006.01)
*A61B 17/22* (2006.01)
*A61B 17/225* (2006.01)

(52) U.S. Cl.
CPC .......... *A61M 1/743* (2021.05); *A61B 17/225* (2013.01); *A61M 1/782* (2021.05); *A61B 2017/22079* (2013.01)

(58) Field of Classification Search
CPC .......... A61M 1/604; A61M 1/68; A61M 1/74; A61M 1/741; A61M 1/7411; A61M 1/7413; A61M 1/7415; A61M 1/743; A61M 1/76; A61M 1/77; A61M 1/774; A61M 1/78; A61M 1/782; A61M 1/80; A61M 1/802; A61M 1/81; A61M 1/82; A61M 1/96; A61M 1/962; A61M 1/98; A61M 1/984; A61M 1/985; A61M 3/0266; A61M 3/0287; A61B 17/225; A61B 17/320016; A61B 2017/22079; A61B 2217/005
See application file for complete search history.

(56) References Cited

U.S. PATENT DOCUMENTS

2006/0047240 A1* 3/2006 Kumar .................. A61M 3/022
604/65

FOREIGN PATENT DOCUMENTS

DE 2814187 A1 * 10/1979 ............. A61B 17/32

* cited by examiner

*Primary Examiner* — Robert A Lynch
(74) *Attorney, Agent, or Firm* — Garrett M. Smith

(57) ABSTRACT

The present disclosure relates to a devices and methods to control suction during medical procedures, and more particularly to medical suction devices, systems, and methods for controlling suction using the portable suction devices/systems during endoscopic procedures. For example, the present disclosure includes a portable suction device in fluid communication with an endoscope system, the portable suction device including: a suction regulator device releasably coupled to and in communication with at least one suction tube of the endoscope system, the at least one suction tube in fluid communication with an endoscope of the endoscope system and a suction source of the endoscope system, wherein the suction regulator device is actuatable to at least one of increase or decrease a suction force within the at least one suction tube.

8 Claims, 20 Drawing Sheets

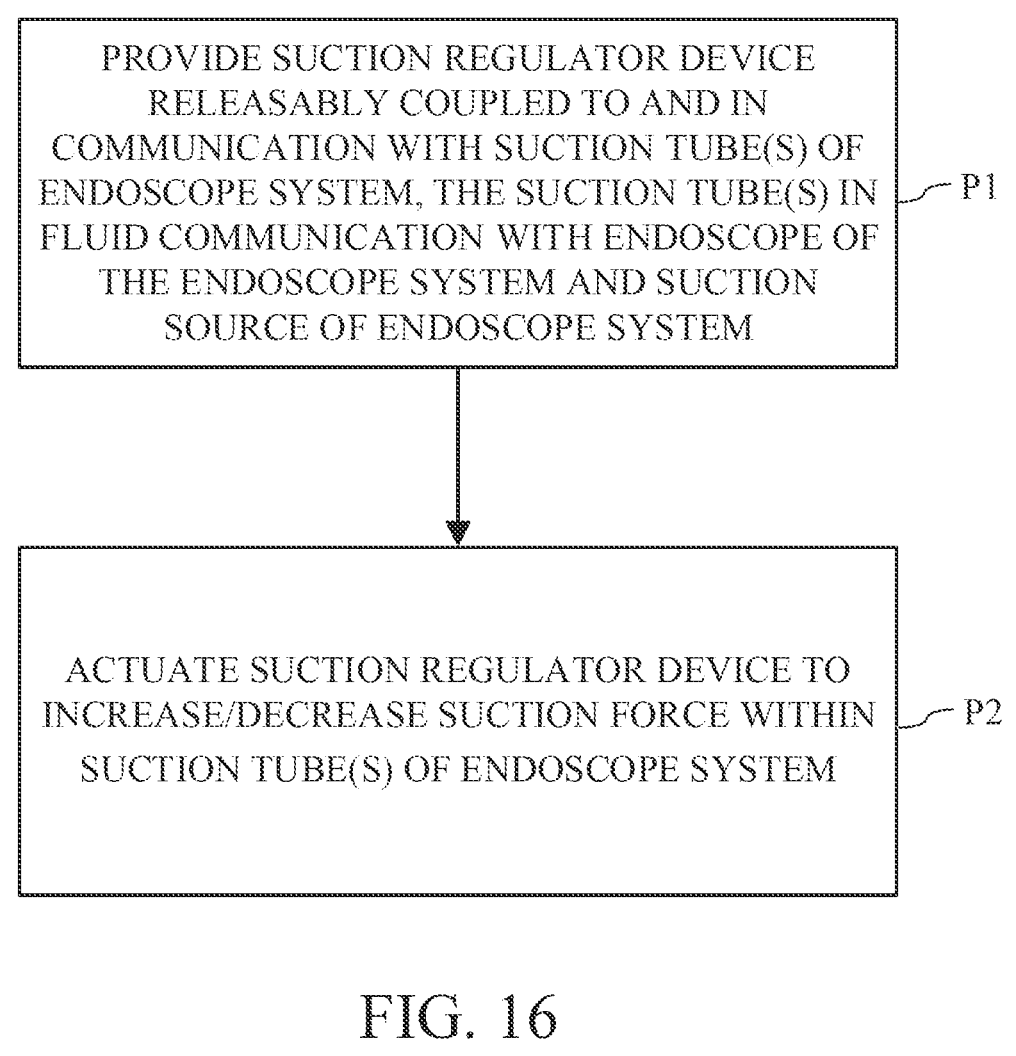

PROVIDE SUCTION REGULATOR DEVICE
RELEASABLY COUPLED TO AND IN
COMMUNICATION WITH SUCTION TUBE(S) OF
ENDOSCOPE SYSTEM, THE SUCTION TUBE(S) IN ⌐ P1
FLUID COMMUNICATION WITH ENDOSCOPE OF
THE ENDOSCOPE SYSTEM AND SUCTION
SOURCE OF ENDOSCOPE SYSTEM

ACTUATE SUCTION REGULATOR DEVICE TO
INCREASE/DECREASE SUCTION FORCE WITHIN ⌐ P2
SUCTION TUBE(S) OF ENDOSCOPE SYSTEM

FIG. 16

PORTABLE SUCTION DEVICES, SYSTEMS, AND METHODS FOR CONTROLLING SUCTION USING SAME

CROSS-REFERNCE TO RELATED APPLICATIONS

The present disclosure claims priority or the benefit under 35 U.S.C. § 119 of U.S. provisional application No. 63/154, 024 filed 26 Feb. 2021, which is herein entirely incorporated by reference.

FIELD OF THE INVENTION

The present disclosure relates generally to controlling suction during medical procedures, and more particularly to portable suction devices, systems, and methods for controlling suction using the portable suction devices/systems during endoscopic procedures.

BACKGROUND

Percutaneous nephrolithotomy is a procedure whereby a needle is inserted into the kidney and dilates a tract for the retrieval of kidney stones. The procedure relies on inserting a sheath through the tract and using fluid irrigation along with a variety of devices to perform lithotripsy, or breaking of stones. The most common methods include combination of ultrasonic/pneumatic lithotripters. These devices have channels through which suction is applied from an external source to remove the stones. Typically, the surgeon requires assistance to modulate the suction by clamping or bending of the suction tubing which leads towards the external suction source (e.g., a wall or floor-based suction device). Such clamping or kinking of tubing is imprecise and requires constant adjustment. For example, too much suction leads to loss of visualization and trapping of air bubbles within the kidney. Conversely, too little suction also affects visualization by the buildup of stone fragments. Additionally, stone fragments often get stuck in suction tubing and cannot be easily removed, thus limiting the effectiveness of the suction device.

There is a continuous need for ureteroscopes that overcome these limitations.

SUMMARY

The present disclosure now provides methods of performing endoscopic procedures including suction control, portable suction devices, systems, and methods for controlling suction using the portable suction devices/systems during one or more endoscopic procedures.

A first aspect of the disclosure provides a suction device such as a portable suction device in fluid communication with an endoscope system. In embodiments, a portable suction device includes: a suction regulator device releasably coupled to and in communication with at least one suction tube of the endoscope system, the at least one suction tube in fluid communication with an endoscope of the endoscope system and a suction source of the endoscope system, wherein the suction regulator device is actuatable to at least one of increase or decrease a suction force within the at least one suction tube.

A second aspect of the disclosure provides a suction system such as a portable suction system, including: a suction regulator device releasably coupled to and in communication with at least one suction tube of an endoscope system, the at least one suction tube in fluid communication with an endoscope of the endoscope system and a suction source of the endoscope system; and a control device in communication with the suction regulator device, the control device actuating the suction regulator device to at least one of increase or decrease a suction force within the at least one suction tube of the endoscope system.

A third aspect of the disclosure provides a method of performing a endoscopic procedure, the method including: providing a suction regulator device releasably coupled to and in communication with at least one suction tube of an endoscope system, the at least one suction tube in fluid communication with an endoscope of the endoscope system and a suction source of the endoscope system; and actuating the suction regulator device to at least one of increase or decrease a suction force within the at least one suction tube of the endoscope system.

A fourth aspect of the present disclosure include a method of treating a patient in need thereof by contacting the patient with an endoscope system of the present disclosure. In embodiments, the contacting is for an effective duration to treat a patient. In embodiments, the treatment method includes actuating the suction regulator device to at least one of increase or decrease a suction force within the at least one suction tube of an endoscope system embodiment of the present disclosure.

The illustrative aspects of the present disclosure are designed to solve the problems herein described and/or other problems not discussed.

BRIEF DESCRIPTIONS OF THE DRAWINGS

FIG. 16 show a flowchart illustrating a process for performing an endoscopic procedure using medial suction devices and/or systems to control the suction, according to embodiments of the disclosure.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

As an initial matter, in order to clearly describe the current disclosure it will become necessary to select certain terminology when referring to and describing relevant components within the disclosure. When doing this, if possible, common industry terminology will be used and employed in a manner consistent with its accepted meaning. Unless otherwise stated, such terminology should be given a broad interpretation consistent with the context of the present application and the scope of the appended claims. Those of ordinary skill in the art will appreciate that often a particular component may be referred to using several different or overlapping terms. What may be described herein as being a single part may include and be referenced in another context as consisting of multiple components. Alternatively, what may be described herein as including multiple components may be referred to elsewhere as a single part.

As used herein, the terms "axial" and/or "axially" refer to the relative position/direction of objects along axis (A), which is substantially parallel with the long axis of the circular shafts, conduits, tubes, channels, etc. discussed herein. As further used herein, the terms "radial" and/or "radially" refer to the relative position/direction of objects along axis (R), which is substantially perpendicular with axis (A) and intersects axis (A) at only one location. Additionally, the terms "circumferential" and/or "circumferentially" refer to the relative position/direction (C) of objects or features along a circumference which surrounds axis (A) but does not intersect the axis (A) at any location. Furthermore, the terms "upstream" and "downstream" refer to the relative direction with respect to fluid flow in a fluid pathway. For example, "upstream" refers to the direction from which the fluid flows, and "downstream" refers to the direction to which the fluid flows.

As discussed herein, the disclosure relates generally to suction control during medical procedures, and more particularly to medical suction devices, systems, and methods for controlling suction using the portable suction devices/systems during endoscopic procedures.

These and other embodiments are discussed below with reference to FIGS. 1-16. However, those skilled in the art will readily appreciate that the detailed description given herein with respect to these Figures is for explanatory purposes only and should not be construed as limiting.

Figure 1:
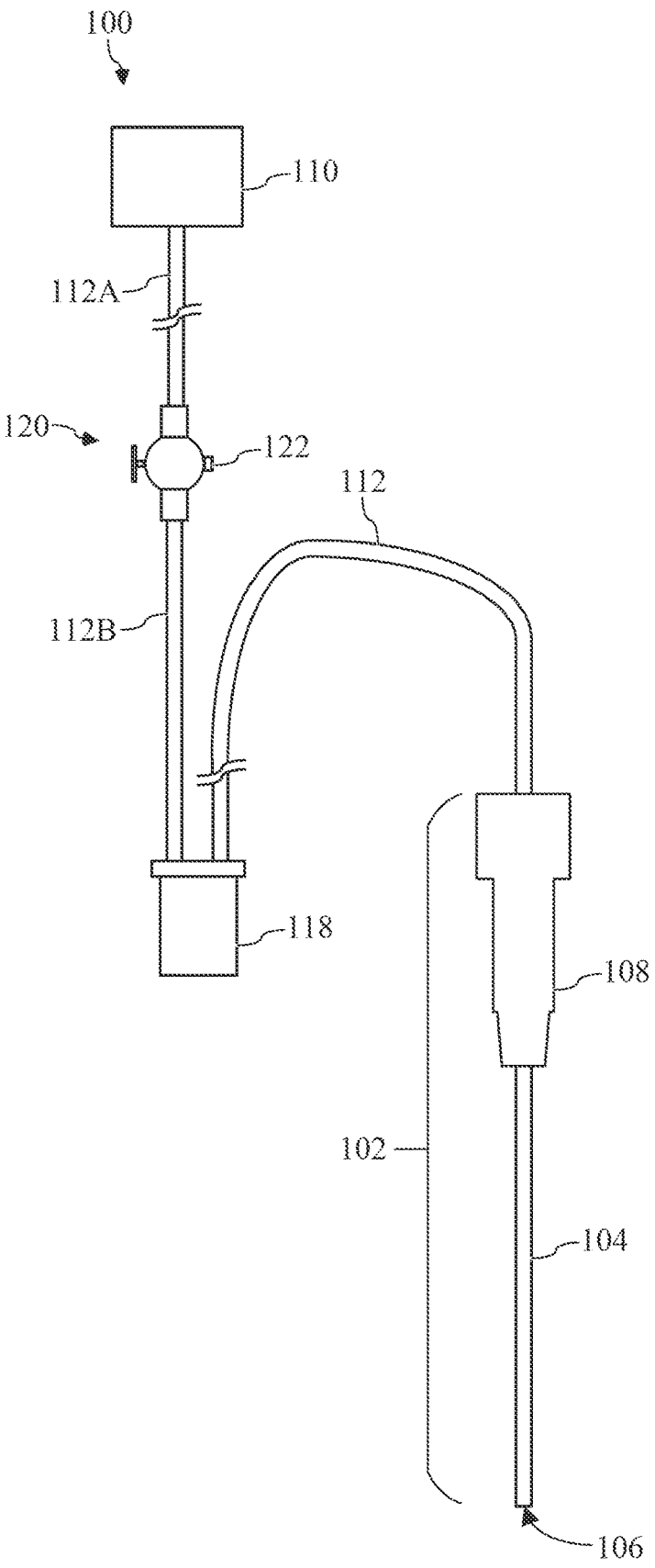
FIG. 1 shows a side view of an endoscope system including an endoscope and suction regulator device, according to embodiments of this disclosure.

FIG. 1 shows a side view of an endoscope system 100. Endoscope system 100 may be used to perform endoscopic procedures and/or processes on a patient or user. For example endoscope system 100 may include a lithotripsy device used to perform a lithotripsy procedure.

In a non-limiting example endoscope system 100 may include an endoscope 102. Endoscope 102 of endoscope system 100 may include a workpiece or shaft 104. In a non-limiting example shaft 104 may include or be formed as the lithotripsy device when endoscope 102 is used to perform a lithotripsy procedure. Shaft 104 may include a working channel 106 extending axially through shaft 104, between a first end and a second end. As discussed herein working channel 106 may provide suction during the endoscopic procedure to remove fluid, discharge, and/or biological debris during the procedure. Shaft 104 of endoscope 102 may include a predetermined length (L). Predetermined length (L) of shaft 104 may be based on, at least in part, the endoscopic procedure performed on the patient, and/or physical characteristics of the patient (e.g., sex of patient, age of patient, patient's lumen for receiving endoscope 102, and so on). Shaft 104 of endoscope 102 may be formed from any suitable material that may be flexible but maintain its shape and/or it's rigidity during the endoscopic procedure. For example, shaft 104 may be formed from a polymer or polymer-based material.

When performing an endoscopic procedure (e.g., lithotripsy) on a patient using endoscope 102, shaft 104 of endoscope 102 may be directly inserted into a lumen of the patient, or may be inserted into an access sheath (not shown) that may be inserted into a patient's lumen.

Endoscope 102 shown in FIG. 1 may also include a handpiece 108. Handpiece 108 may be releasably coupled to shaft 104. More specifically, handpiece 108 may be releasably coupled to a first end of shaft 104 of endoscope 102. As discussed herein, handpiece 108 may provide access to and/or may allow a user to control the movement and/or position of shaft 104 (and the device formed therein) and/or other features included in endoscope 102 (e.g., camera) when performing the endoscopic procedure.

As discussed herein, some endoscopic procedures performed using endoscope system 100 may require suction to remove fluid, discharge, and/or biological debris during the procedure. As such, endoscope system 100 shown in FIG. 1 may also include a suction source 110 and at least one suction tube 112 fluidly coupling endoscope 102 to suction source 110. In the non-limiting example, a plurality of suction tubes 112 may extend between and may fluidly couple suction source 110 and endoscope 102. Suction source 110 may be formed has any suitable device, apparatus, assembly, and or system that may provide a suction force through tubes 112 and shaft 104 of endoscope 102 during the endoscopic procedure, as discussed herein. For example, suction source 110 may be a portable suction device or may be a wall mounted unit of a larger system. Additionally, the plurality of suction tubes 112 may be formed as any suitable conduit and/or Cannula that may provide the suction force to shaft 104 of endoscope 102 and/or remove the fluid/biological debris during the endoscopic procedure. In a non-limiting example the plurality of suction tubes 112 may be formed from a flexible, polymer material.

As shown in FIG. 1, endoscope system 100 may also include a specimen container 118. Specimen container 118 may be positioned between endoscope 102 and suction source 110. More specifically specimen container 118 may be in fluid communication with both endoscope 102 and suction source 110 via suction tubes 112, and may be positioned downstream from endoscope 102 and upstream of suction source 110. Specimen container 118 may be formed as any suitable apparatus, component, and/or system that may collect biological specimens or debris during the procedure performed using endoscope system 100. In embodiments, a treatment of the present disclosure includes a procedure performed using endoscope 100, such as lithotripsy, wherein a specimen container 118 collects debris, such as kidney stones, removed from the patient via endoscope 102 and the suction force applied by suction source 110.

In embodiments, in order to control and/or adjust the suction force through endoscope system 100 during the procedure, a portable suction device 120 may be included within endoscope system 100. For example, and as shown in FIG. 1, a suction regulator device 122 may be included within endoscope system 100. Suction regulator device 122 may be releasably coupled to and in communication with at least one suction tube 112 of endoscope system 100. In the non-limiting example shown in FIG. 1, suction regulator device 122 may be in direct fluid communication with a first suction tube 112A and a second suction tube 112B. As shown, first suction tube 112A may be in direct fluid communication with suction source 110 and second suction tube 112B may be in direct fluid communication with specimen container 118. As such, suction regulator device 122 may be positioned between suction source 110 and specimen container 118. Additionally, in embodiments, suction regulator device 122 is positioned downstream from specimen container 118 and upstream from suction source 110, respectively.

In embodiments, suction regulator device 122 may be formed as any suitable device, component, and/or assembly that may be actuatable to at least one of increase or decrease the suction force within the suction tube 112 and/or through endoscope system 100. As shown in the non-limiting example suction regulator device 122 may include or be formed as an adjustable valve, such as a stopcock or ball valve. In other non-limiting examples discussed herein (e.g., FIG. 3), suction regulator device 122 may be formed as an clamping component. The configuration and/or formation of suction regulator device 122 may determine whether suction regulator device 122 is in fluid communication with portions of endoscope system 100, or merely in communication and/or coupled to portions of endoscope system 100. For example, where suction regulator device 122 includes an adjustable valve, the adjustable valve forming suction regulator device 122 may be directly coupled to and/or may be in direct fluid communication with portions of endoscope system 100 (e.g., suction tubes 112). As discussed herein, where suction regulator device 122 is formed from an clamping component, the clamping component forming suction regulator device 122 may be coupled to and/or positioned on portions of endoscope system 100 (e.g., coupled to suction tubes 112) (see e.g., FIGS. 4 and 5).

In embodiments, during operation suction regulator device 122 may be adjusted and/or actuated to open or close the passageway in suction tubes 112, which in turn may increase or decrease the amount of suction force applied in suction tube 112 and/or endoscope system 100. Furthermore, suction regulator device 122 may be variably actuated such that endoscope 102 and/or suction tubes 112 may experience no suction force (e.g., completely off or blocked by suction regulator device 122), full suction force (e.g., suction regulator device 122 completely on), or partial suction force (e.g., suction regulator device 122 partially opened/closed).

Figure 2:
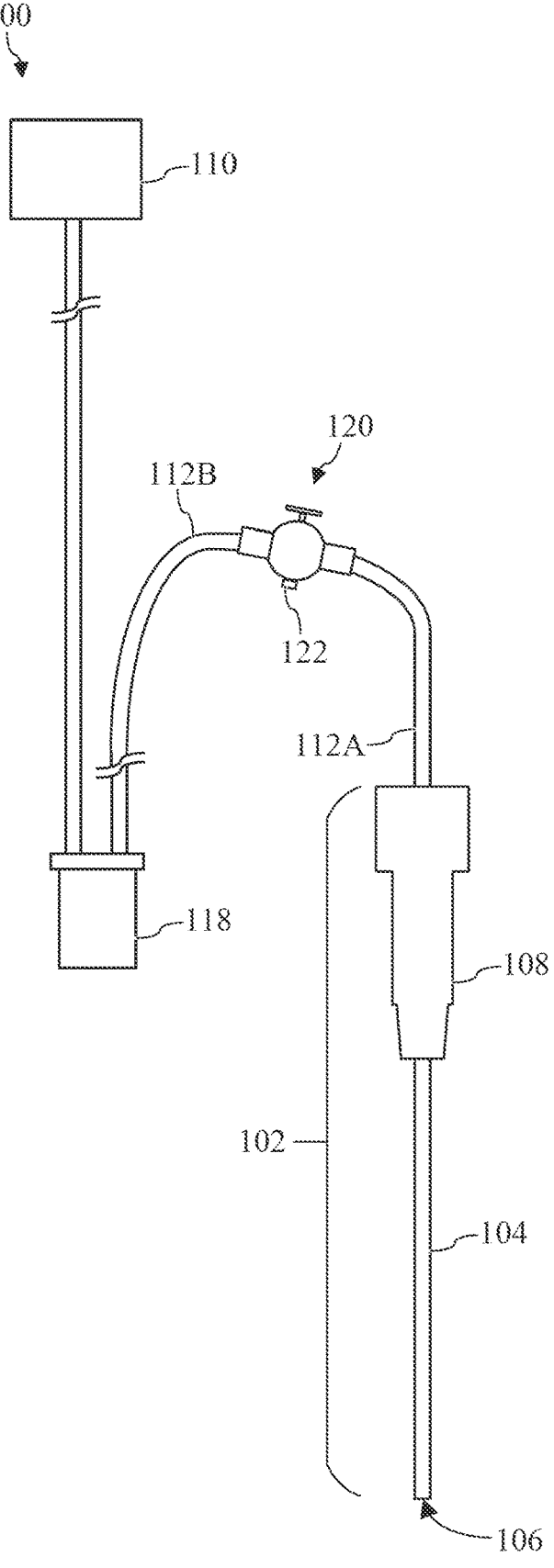
FIG. 2 shows a side view of an endoscope system including an endoscope and suction regulator device, according to additional embodiments of the disclosure.

FIG. 2 shows another non-limiting example of endoscope system 100 including suction regulator device 122. In embodiments, suction regulator device 122 is positioned upstream from specimen container 118 and downstream from handpiece 108, respectively. It is understood that similarly numbered and/or named components may function in a substantially similar fashion. Redundant explanation of these components has been omitted for clarity.

As shown in FIG. 2, suction regulator device 122 may be releasably coupled to and in communication with at least one suction tube 112 of endoscope system 100. In the non-limiting example, suction regulator device 122 may be in direct fluid communication with a first suction tube 112A and a second suction tube 112B. As shown, first suction tube 112A may be in direct fluid communication with endoscope 102 and second suction tube 112B may be in direct fluid communication with specimen container 118. As such, suction regulator device 122 may be positioned between endoscope 102 and specimen container 118. Additionally, suction regulator device 122 is positioned downstream from endoscope 102 and upstream from specimen container 118, respectively. Similar to the non-limiting example shown and discussed herein with respect to FIG. 1, suction regulator device 122 may be formed as or may include an adjustable valve. As such, the adjustable valve forming suction regulator device 122 may be directly coupled to and/or may be in direct fluid communication with first suction tube 112A and second suction tube 112B of endoscope system 100.

Figure 3:
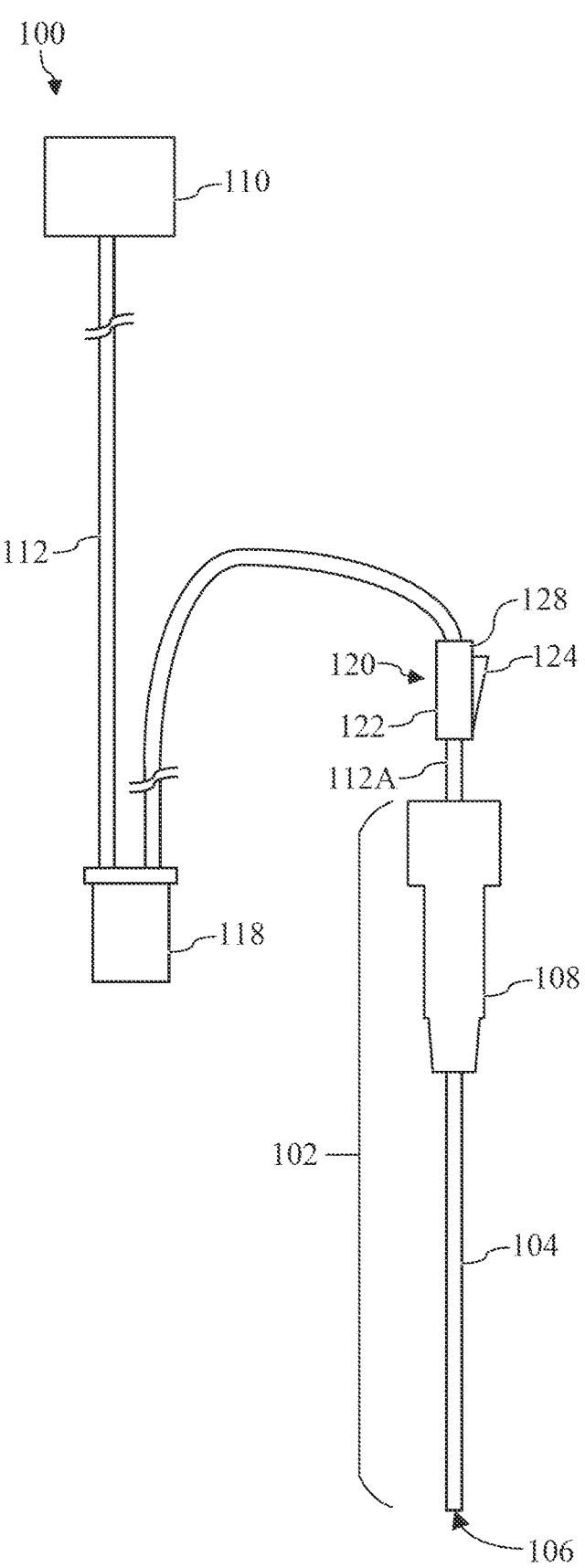
FIG. 3 shows a side view of an endoscope system including an endoscope and suction regulator device, according to further embodiments of the disclosure.

FIG. 3 shows another non-limiting example of endoscope system 100 including suction regulator device 122. In the non-limiting example, suction regulator device 122 may be formed from an actuatable clamping component. Briefly turning to FIGS. 4 and 5, clamping component forming suction regulator device 122 may be in communication with, positioned on, substantially surround, and/or be coupled to the single, first suction tube 112A fluidly coupling endoscope 102 and specimen container 118. That is, suction regulator device 122 of FIG. 3 may be in communication with first suction tube 112A in direct fluid communication with endoscope 102 and specimen container 118. As such, suction regulator device 122 may be positioned between endoscope 102 and specimen container 118, and/or may be positioned downstream of endoscope 102 and upstream from specimen container 118, respectively.

Figure 4:
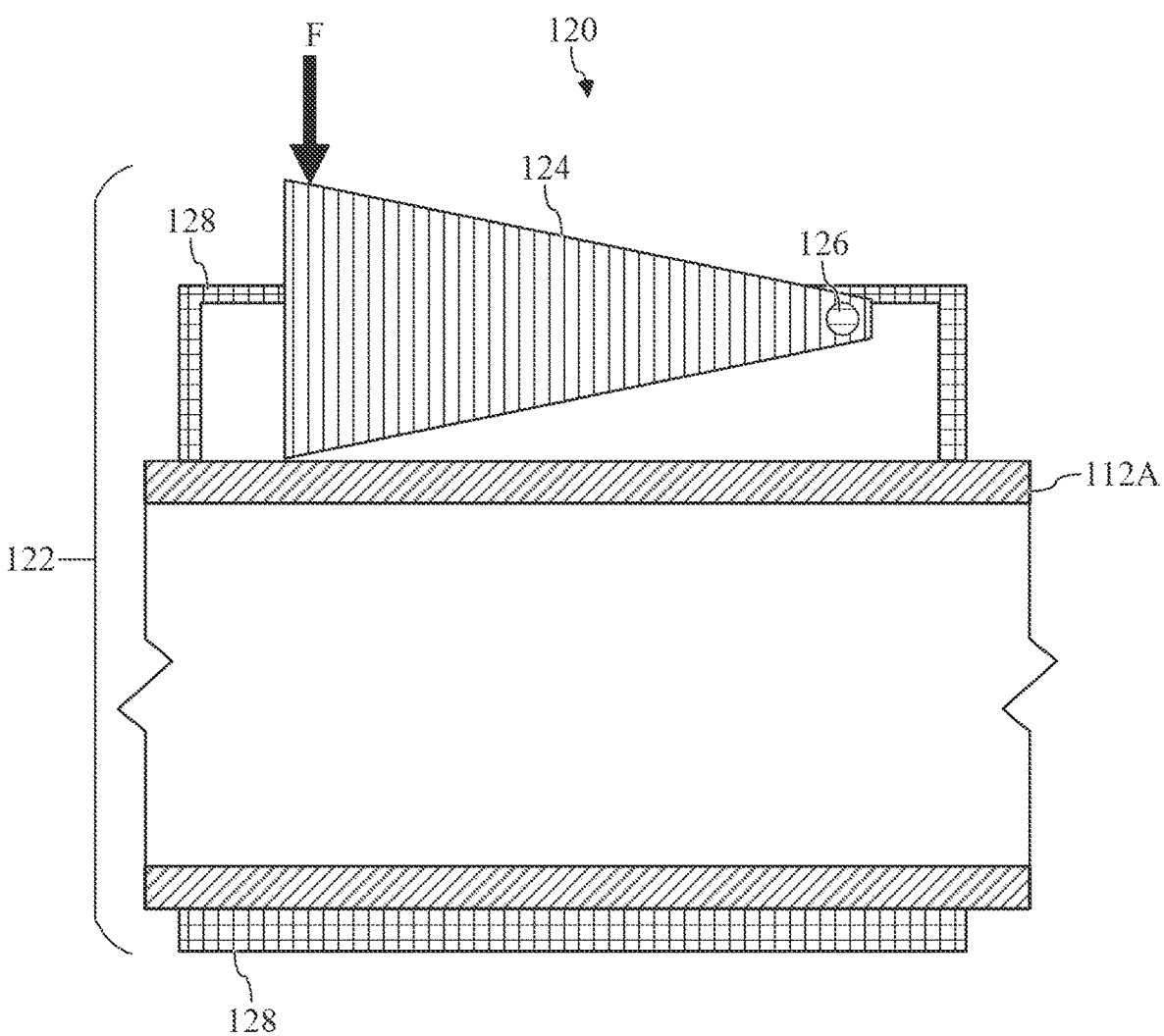
FIG. 4 shows a side cross-sectional view of the suction regulator device of FIG. 3 in an unactuated positioned, according to embodiments of the disclosure.
Figure 5:
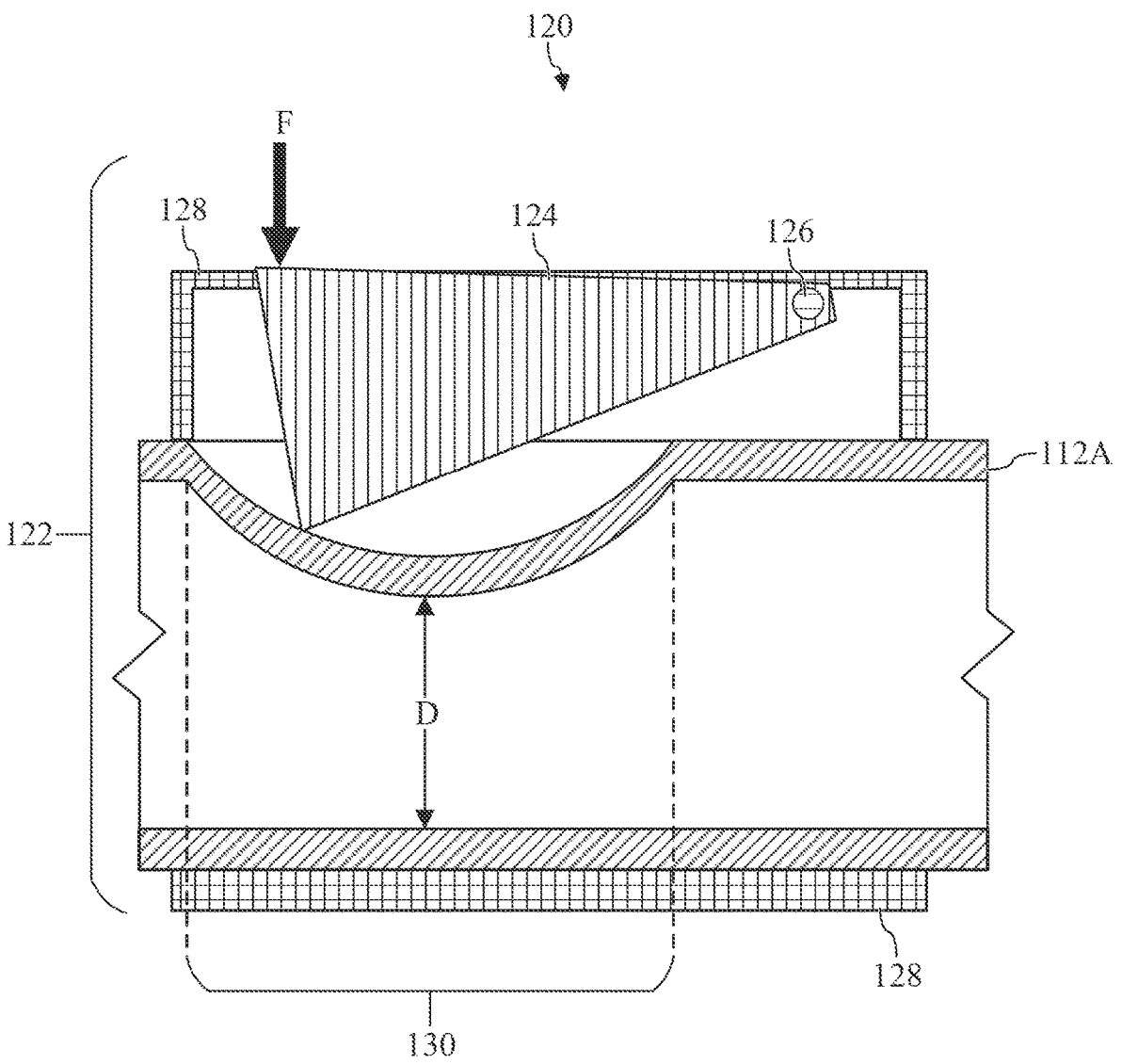
FIG. 5 shows a side cross-sectional view of the suction regulator device of FIG. 3 in an actuated positioned, according to embodiments of the disclosure.

Turning to FIGS. 4 and 5, side cross-sectional views of a portion of first suction tube 112A and suction regulator device 122 are shown. Specifically, FIG. 4 shows suction regulator device 122 in an unactuated position, while FIG. 5 shows suction regulator device 122 in an actuated position.

In the non-limiting example, suction regulator device 122 including or configured as a actuatable clamping component may include a contacting pad 124 pivotable coupled to a pivot point 126. Contact pad 124 may be configured to rotate in a direction (R) about pivot point 126 which may be fixed and/or may affix or couple one portion/end of contact pad 124 to housing 128 of actuatable clamping component forming suction regulator device 122. In the non-limiting example shown in FIG. 4, housing 128 of suction regulator device 122 may be coupled to, may substantially surround, and/or may receive first suction tube 112A. Additionally, contact pad 124 may contact and/or rest on, but not deform a portion of first suction tube 112A in the unactuated position. In the unactuated position of contact pad 124 for clamping component shown in FIG. 4, the suction force experienced and/or applied within suction tube 112A, and/or shaft 104 of endoscope 102 may be unaffected and/or unaltered (e.g., 100% suction force).

Turning to FIG. 5, contact pad 124 of clamping component forming suction regulator device 122 is shown in an actuated positioned. That is, contact pad 124 of clamping component may be actuation and/or rotation toward suction tube 112A. Contact pad 124 may be actuated and/or rotated by a user of endoscope system 100 applying a force (F) to the exposed portion of contact pad 124 protruding or extending from housing 128 (see, FIG. 4). Actuating/rotating contact pad 124 toward suction tube 112A may result in the deformation, bending, and/or squeezing of a portion 130 of suction tube 112A. That is, actuated contact pad 124 may be formed into and consequently deform suction tube 112A. The deformation of portion 130 of suction tube 112A by contact pad 124 of clamping component forming suction regulator device 122 may reduce the diameter (D) and/or cross-sectional area in the deformed portion 130. Deforming portion 130, and in turn reducing the diameter (D) of portion 130 of suction tube 112A, may reduce the suction force experienced and/or applied within suction tube 112A, and/or shaft 104 of endoscope 102. The suction force may be further reduced by actuating contact pad 124 further into portion 130 of suction tube 112A. Alternatively, the suction force may be increased by releasing contact pad 124 and/or reduce the force applied to contact pad 124. Releasing/ reducing the force (F) applied to contact pad 124 may reduce the displacement of contact pad 124 and/or may rotate contact pad 124 back to or close to its unactuated position. This in turn may increase the diameter (D) of deformed portion 130.

In addition to reducing the suction force experience and/or applied within suction tube 112A, contact pad 124 of clamping component forming suction regulator device 122 may also crush, break, and/or crumble biological debris or specimens (e.g., kidney stones) that may flow through suction tubes 112 before reaching specimen container 118. That is, contact pad 124 deforming suction tube 112A in an actuated state may also apply a force to biological debris that may flow through and/or be suctioned-up through suction tube 112A to break-up or further crush the debris. As such, suction regulator device 122 may prevent biological debris or specimens from clogging suction tubes 112A during the procedure performed using endoscope system 100.

Figure 6:
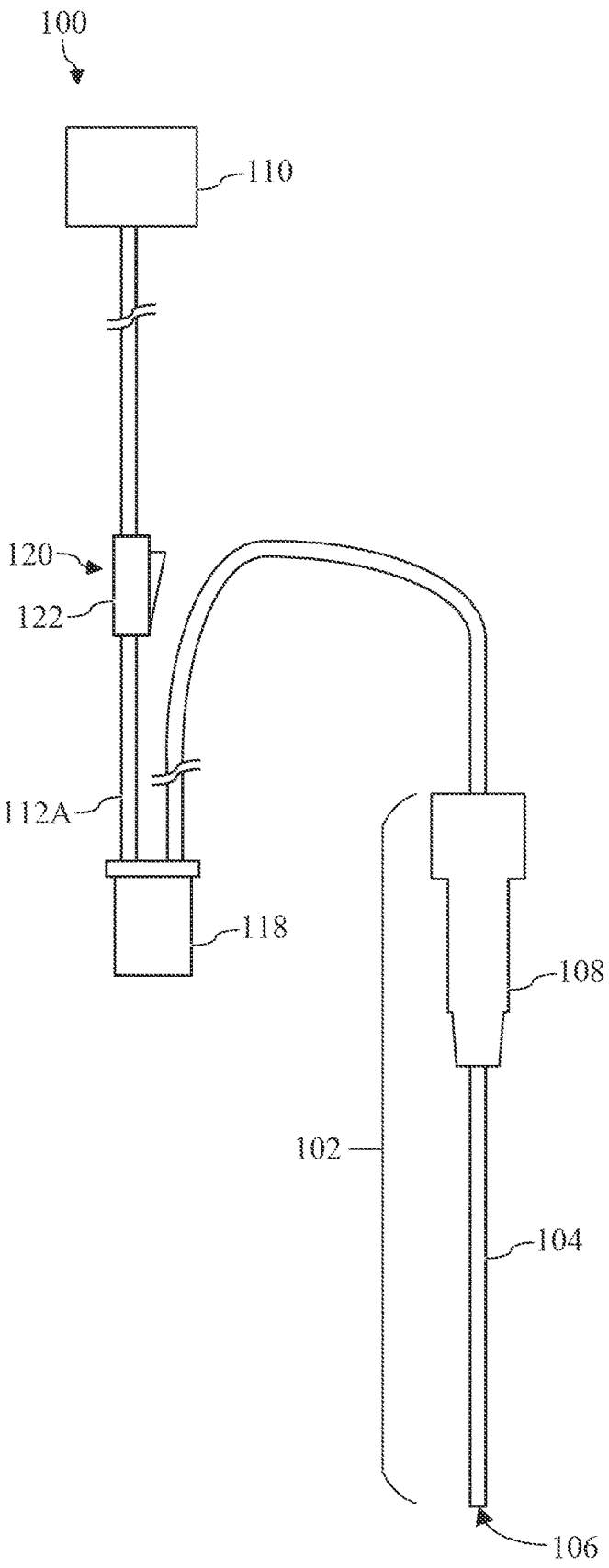
FIG. 6 depicts an endoscope system of the present disclosure including an endoscope and suction regulator device in accordance with an embodiment of the present disclosure.
Figure 7:
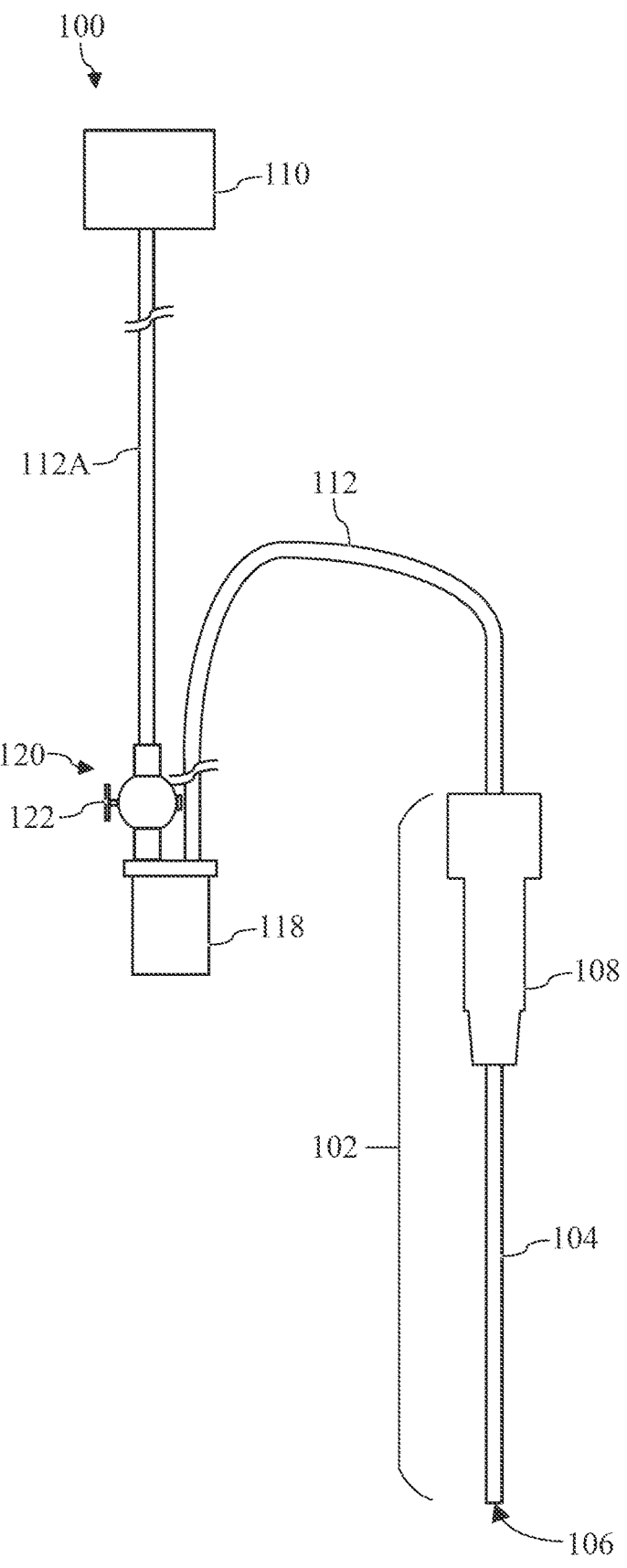
FIG. 7 depicts an endoscope system of the present disclosure including an endoscope and suction regulator device in accordance with an embodiment of the present disclosure.
Figure 8:
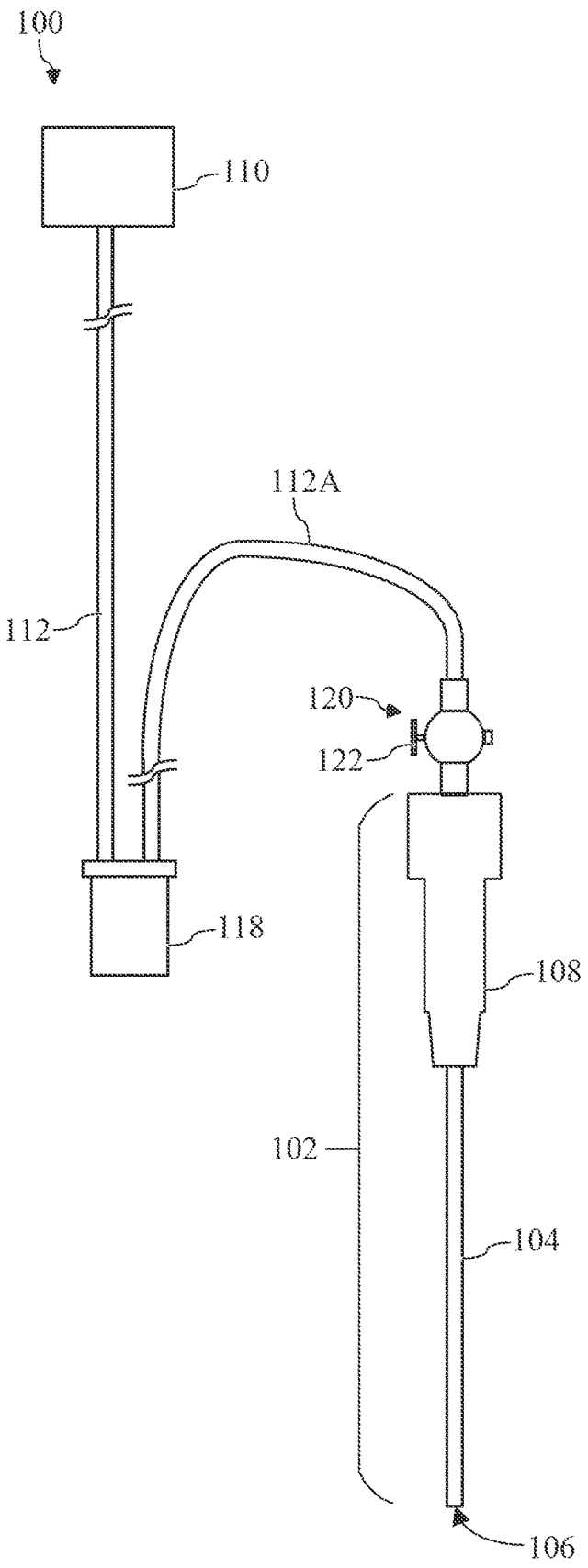
FIG. 8 depicts an endoscope system of the present disclosure including an endoscope and suction regulator device in accordance with an embodiment of the present disclosure.

FIGS. 6-8 show additional non-limiting examples of endoscope system 100 including suction regulator device 122. It is understood that similarly numbered and/or named components may function in a substantially similar fashion. Redundant explanation of these components has been omitted for clarity.

In the non-limiting example shown in FIG. 6, suction regulator device 122 may be formed from an actuatable clamping component in communication with, positioned on, substantially surround, and/or be coupled to the single, first suction tube 112A fluidly coupling suction source 110 and specimen container 118. That is, suction regulator device 122 may be in communication with first suction tube 112A in direct fluid communication with suction source 110 and specimen container 118. As shown, suction regulator device 122 may be positioned between suction source 110 and specimen container 118, and/or may be positioned downstream of specimen container 118 and upstream from suction source 110, respectively.

In the non-limiting example shown in FIG. 7, suction regulator device 122 may be formed from an adjustable valve in communication with specimen container 118 and first suction tube 112A fluidly coupled to suction source 110 and suction regulator device 122. That is, suction regulator device 122 may be positioned between and may be in direct fluid communication with specimen container 118 and first suction tube 112A in direct fluid communication with suction source 110. As shown, suction regulator device 122 may be positioned between suction source 110 and specimen container 118, and/or may be positioned downstream of specimen container 118 and upstream from suction source 110, respectively. In another non-limiting example (not shown), suction regulator device 122 may be positioned between and may be in direct fluid communication with suction source 110 and first suction tube 112A in direct fluid communication with specimen container 118.

As shown in FIG. 8, suction regulator device 122 may be formed from an adjustable valve in communication with endoscope 102 and first suction tube 112A fluidly coupled to specimen container 118 and suction regulator device 122. More specifically, suction regulator device 122 may be positioned between and may be in direct fluid communication with endoscope 102 (e.g., handpiece 108) and first suction tube 112A in direct fluid communication with specimen container 118. As shown in the non-limiting example, suction regulator device 122 may be positioned between endoscope 102 and specimen container 118, and/or may be positioned downstream of endoscope 102 and upstream from specimen container 118, respectively. In another non-limiting example (not shown), suction regulator device 122 may be positioned between and may be in direct fluid communication with specimen container 118 and first suction tube 112A in direct fluid communication with endoscope 102.

FIGS. 9-15 show various non-limiting examples of endoscope system 100 embodiments including a portable suction system 132 including suction regulator device 122. It is understood that similarly numbered and/or named components may function in a substantially similar fashion. Redundant explanation of these components has been omitted for clarity.

In the non-limiting examples, portable suction system 132 included in endoscope system 100 may include suction regulator device 122. Suction regulator device 122 may for be formed as and/or may include an adjustable valve or an impingement component, as similarly discussed herein with respect to FIGS. 1-8, or may be formed from any other suitable configuration that may allow for the controlling of the suction force during a procedure as discussed herein. In embodiments, suction regulator device 122 may be releasably coupled to and/or in communication with suction tube(s) 112 of endoscope system 100, as similarly discussed herein. In the non-limiting examples, suction regulator device 122 may also be configured and/or formed as a motorized device or a manual device. As discussed herein, the formation of suction regulator device 122 as a motorized device where manual device may be dependent upon additional portions, components, devices, and/or features of portable suction system 132.

In embodiments, portable suction system 132 may also include a control device 134. Control device 134 may be in communication with suction regulator device 122. More specifically, and dependent upon the configuration of suction regulator device 122 (e.g., motorized, manual), control device 134 may be electrically coupled to and/or in electronic communication with suction regulator device. Alternatively, control device 134 maybe couple 2 and/or (mechanically) in communication with suction regulator device 122. Control device 134 of portable suction system 132 may actuate or instruct suction regulator device 122 to be actuated to increase and/or decrease the suction force within the at least one suction tube 112 of endoscope system 100.

Additionally in the non-limiting examples, control device 134 of portable suction system 132 may be releasably coupled to endoscope 102 of endoscope system 100. For example, and turning to FIG. 9, control device 134 maybe releasably coupled to handpiece 108 of endoscope 102. Control device 134 maybe releasably coupled to handpiece 108 of endoscope 102 using any suitable releasable coupling system, apparatus, and/or component. In the non-limiting example shown in FIG. 9, control device 134 may be releasably coupled to handpiece 108 of endoscope 102 using a plurality of hook-and-loop (e.g., Velcro®) straps 135. In other non-limiting examples, controlled device may be releasably coupled to handpiece 108 using snap-fits, elastic cordage, compressive sleeves, clamps, adhesives or adhesive materials, and the like. Releasably coupling control device 134 to handpiece 108 of endoscope 102 may allow the user (e.g., surgeon) to simultaneously perform the procedure using endoscope 102 and control/adjust the suction force provided by suction source 110 during the procedure.

Figure 9:
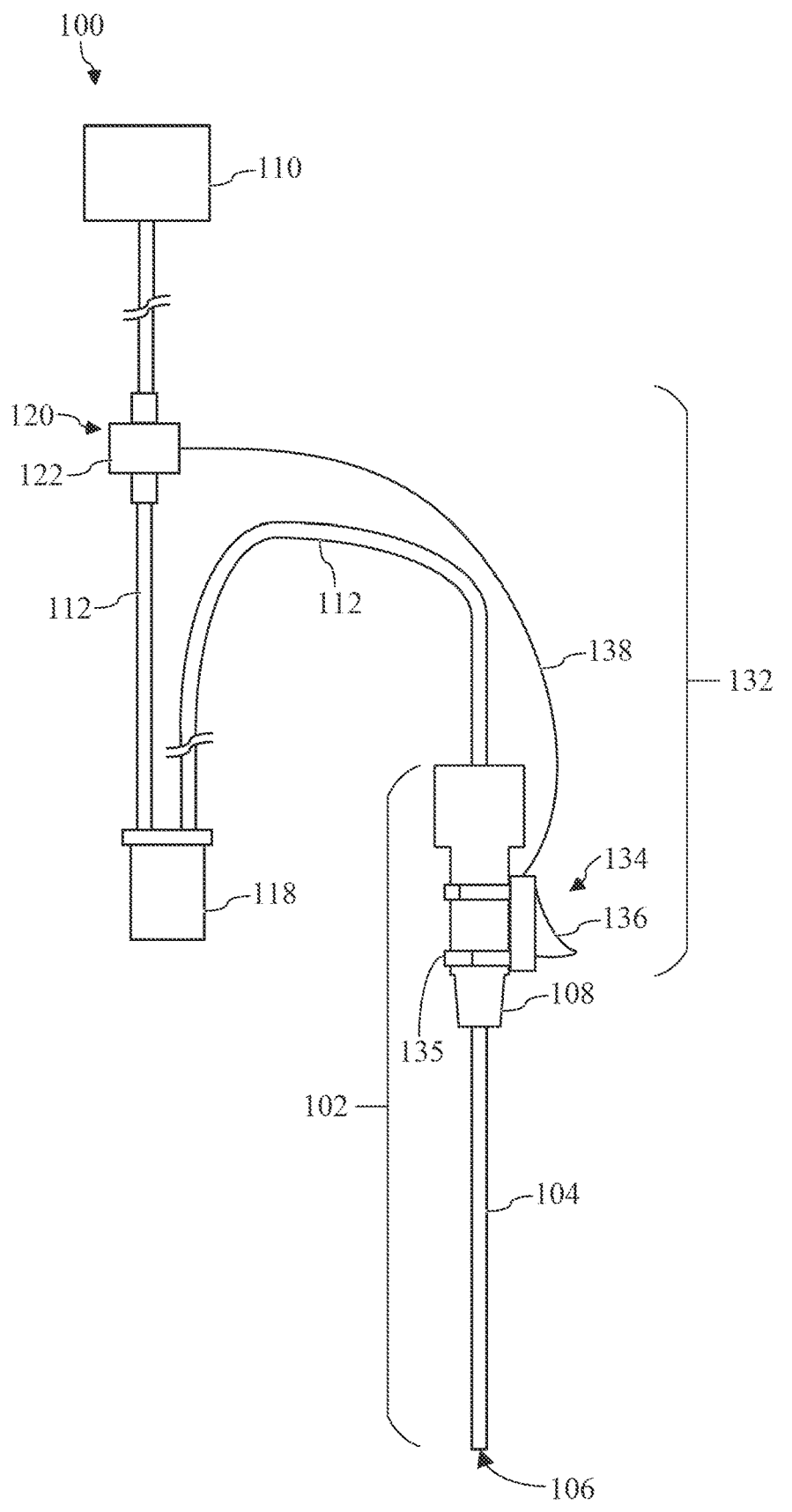
FIG. 9 depicts a side view of an endoscope system embodiment of the present disclosure.

In the non-limiting example shown in FIG. 9, control device 134 may include and/or be formed as a variable trigger component 136. Variable trigger component 136 forming control device 134 may be mechanically coupled to and/or in communication with suction regulator device 122 via a tension cable 138. In this example, suction regulator device 122 may be formed as an impingement component that may be engaged and/or actuated based on the operation of variable trigger component 136. That is, impingement component forming suction regulator device 122 may be formed as a manual device that may be actuated and/or may deform suction tube 112 based on the operation and/or engagement of variable trigger component 136. In this example, engaging and/or squeezing variable trigger component 136 may create a force on tension cable 138 which in turn may actuate suction regulator device 122 to deform suction tube 112, as similarly discussed herein with respect to FIG. 5. The user of portable suction system 132, and specifically control device 134, may continuously adjust the suction force provided by suction source 110 by squeezing and/or engaging variable trigger component 136.

Figure 10A:
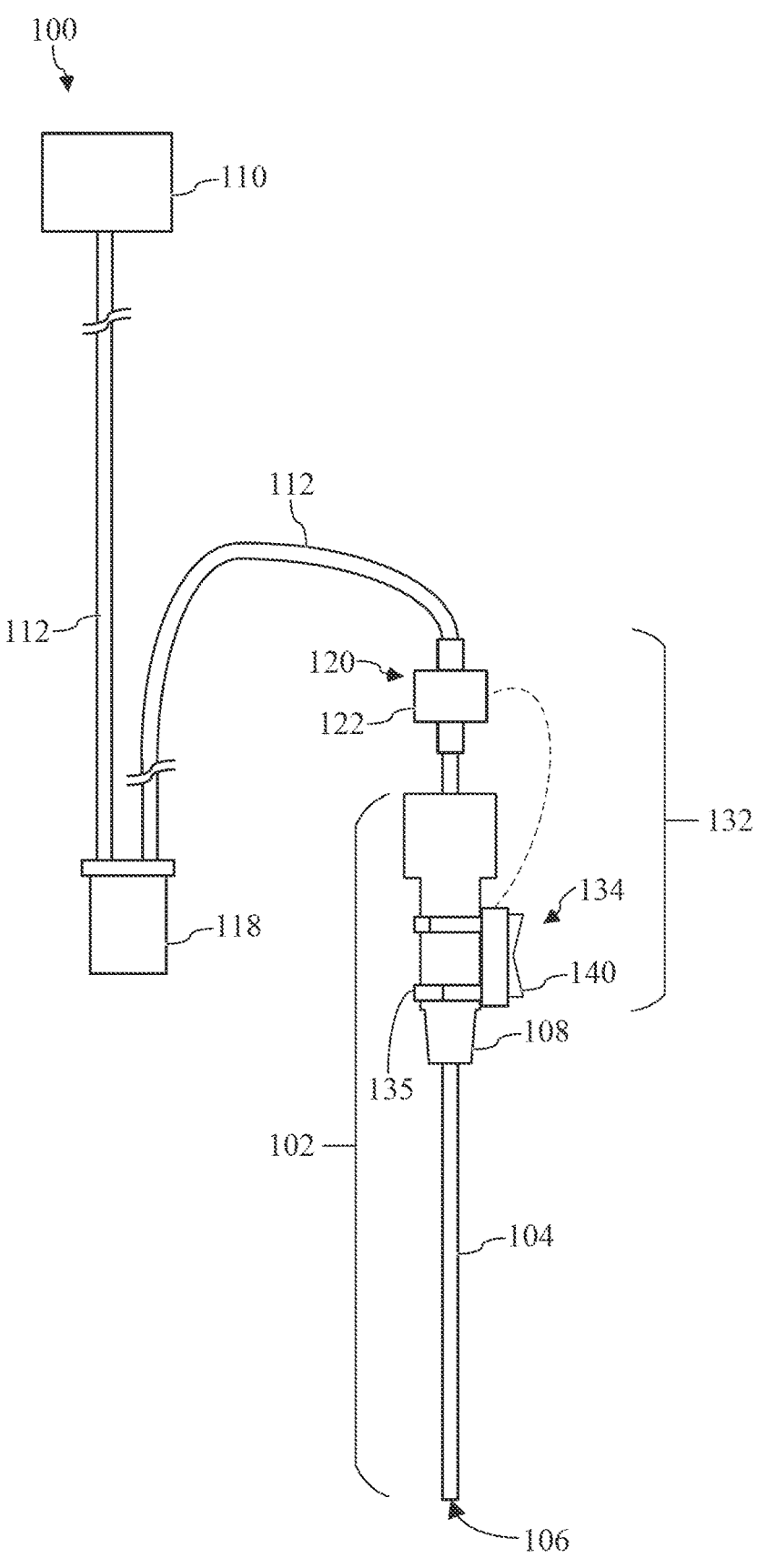
FIGS. 10A and 10B depict side views of endoscope system embodiments of the present disclosure.
Figure 10B:
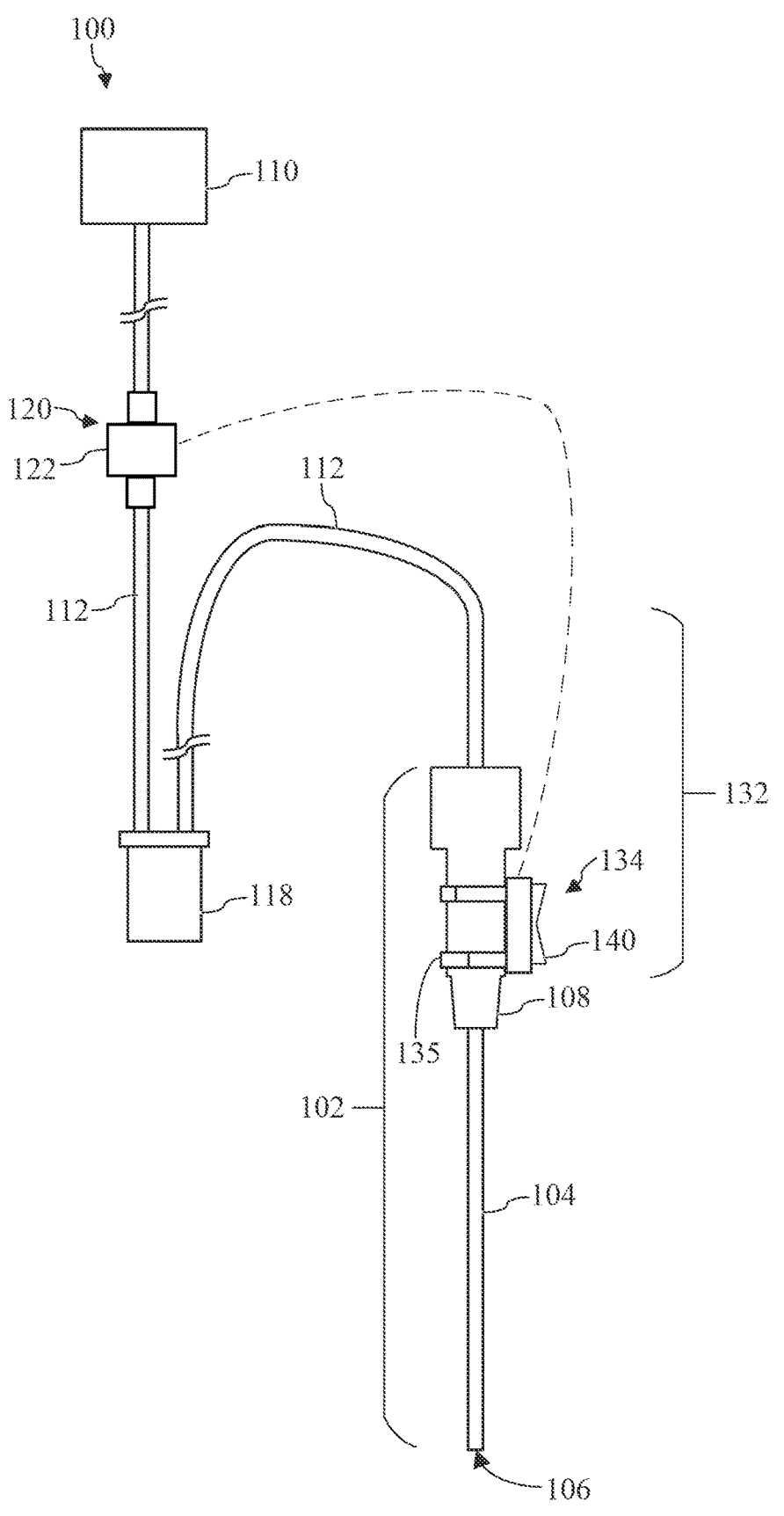

Turning to FIGS. 10A and 10B, control device 134 may include and/or may be formed as a toggle switch 140. Toggle switch 140 maybe releasably coupled to handpiece 108 of endoscope 102, as similarly discussed herein. In the non-limiting example, toggle switch 140 may be electrically coupled to and/or in electronic communication with suction regulator device 122 (shown as a dotted line in FIGS. 10A and 10B). In the example, toggle switch 140 may be electrically hardwired, or may be wirelessly coupled and in communication with suction regulator device 122. As such, suction regulator device 122 shown in FIGS. 10A and 10B may be formed or configured as a motorized device that may be actuated based on signals or input received from toggle switch 140. Toggle switch 140 maybe wirelessly coupled to and in communication with suction regulator device 122 using any suitable wireless communication assembly and/or technique. For example, toggle switch 140 maybe wirelessly coupled to suction regulator device 122 using Bluetooth technology. In the example where toggle switch 140 is wirelessly coupled to suction regulator device 122, a power source (not shown) may be connected to the toggle switch 140 and/or suction regulator device 122. As shown in FIG. 10A, in embodiments, suction regulator device 122 is positioned upstream from specimen container 118 and downstream from handpiece 108. As shown in FIG. 10B, in embodiments, suction regulator device 122 is positioned downstream from specimen container 118.

Figure 11A:
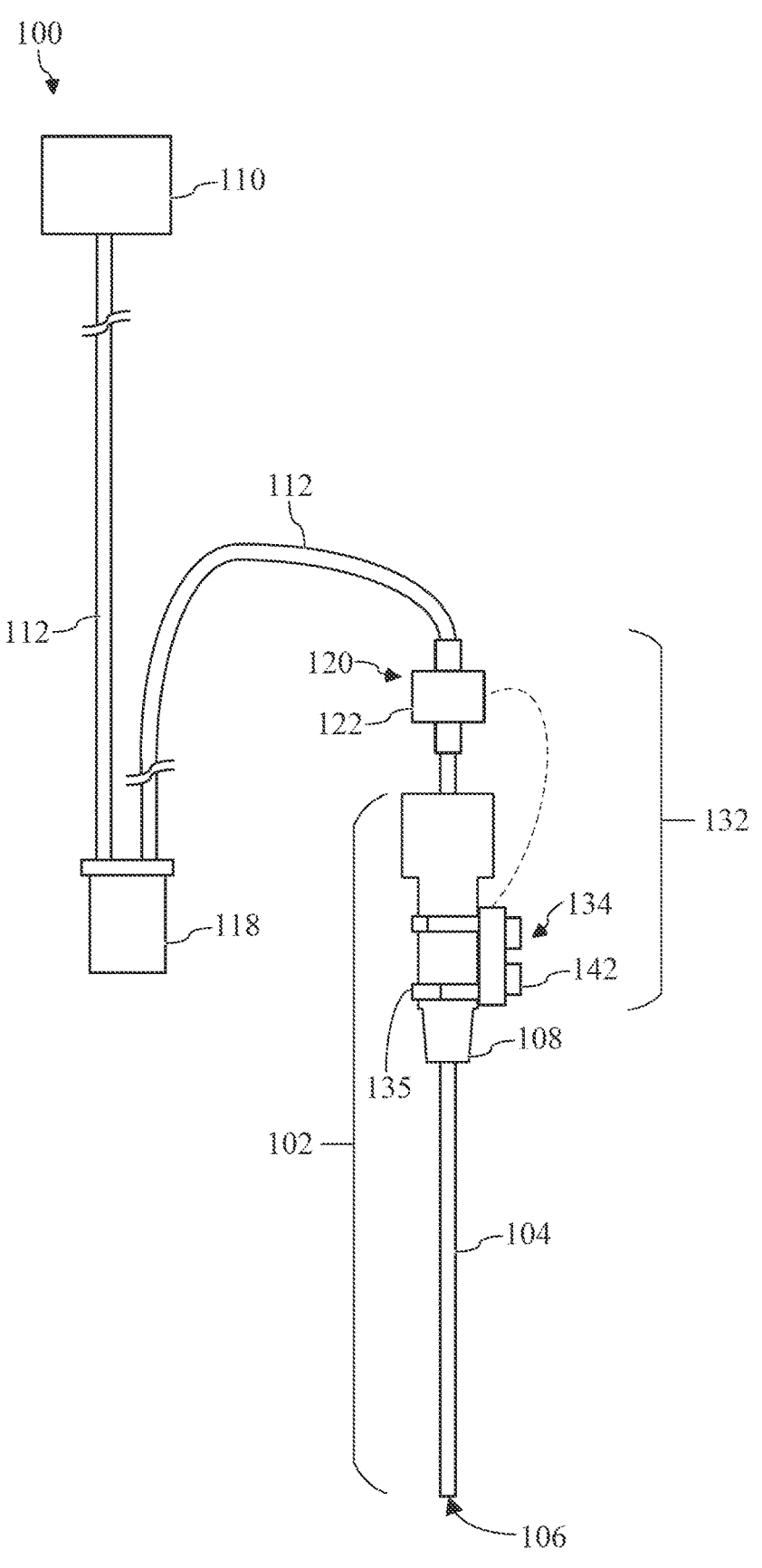
FIGS. 11A and 11B depict side views of endoscope system embodiments of the present disclosure.
Figure 11B:
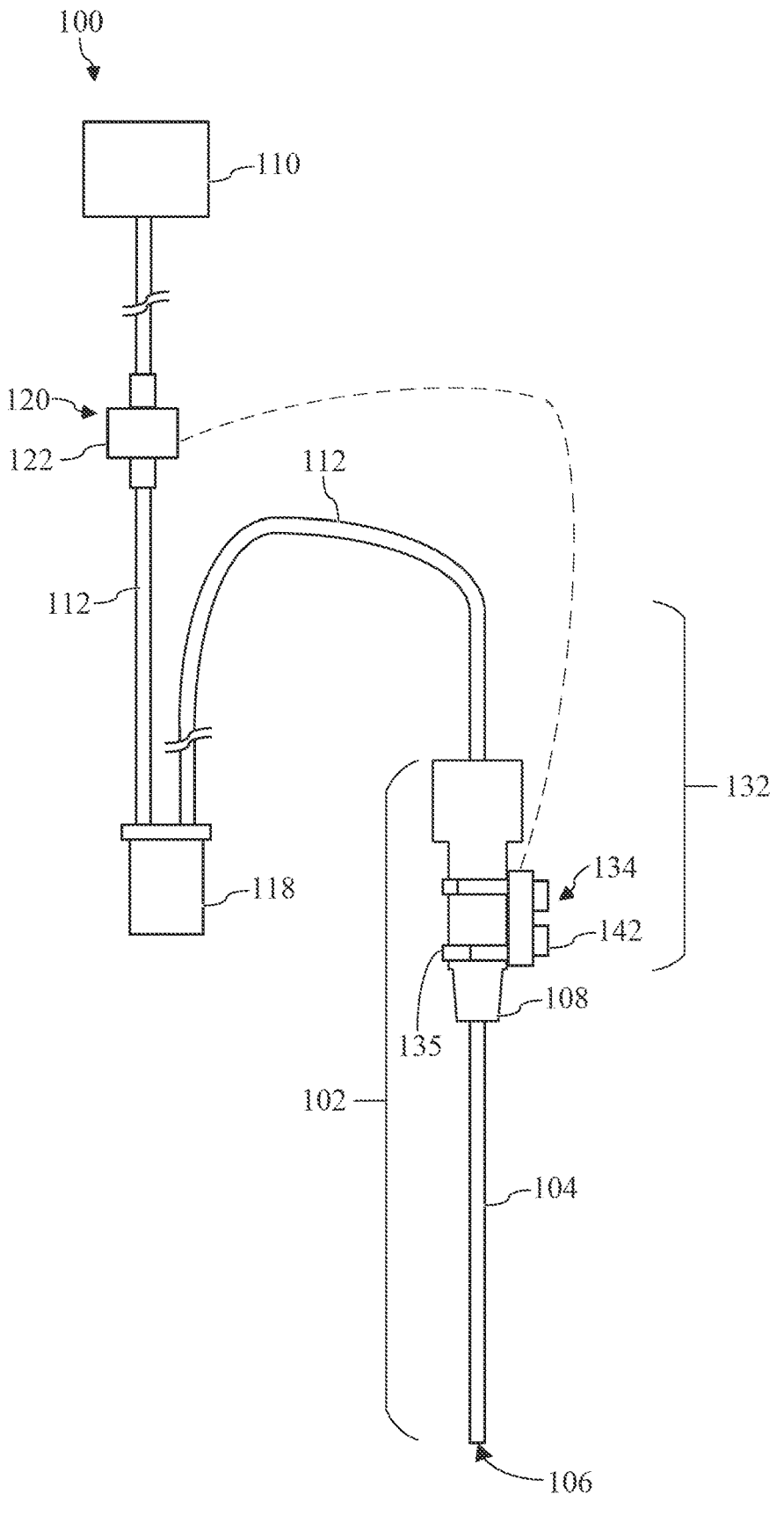

FIGS. 11A, 11B, 12A and 12B show additional non-limiting examples of control device 134 for portable suction system 132. In the example shown in FIGS. 11A and 11B, control device 134 releasably coupled to handpiece 108 of endoscope 102 maybe formed as a push button switch 142. Push button switch 142 may include at least two distinct buttons which may allow the user of endoscope 102 the ability to control and/or adjust the suction force provided by suction source 110, as similarly discussed herein. As shown in FIG. 11A, in embodiments, suction regulator device 122 is positioned upstream from specimen container 118 and downstream from handpiece 108. As shown in FIG. 11B, in embodiments, suction regulator device 122 is positioned downstream from specimen container 118. In the non-limiting example, push button switch 142 may be electrically coupled to and/or in electronic communication with suction regulator device 122 (shown as a dotted line in FIGS. 11A and 11B).

Figure 12A:
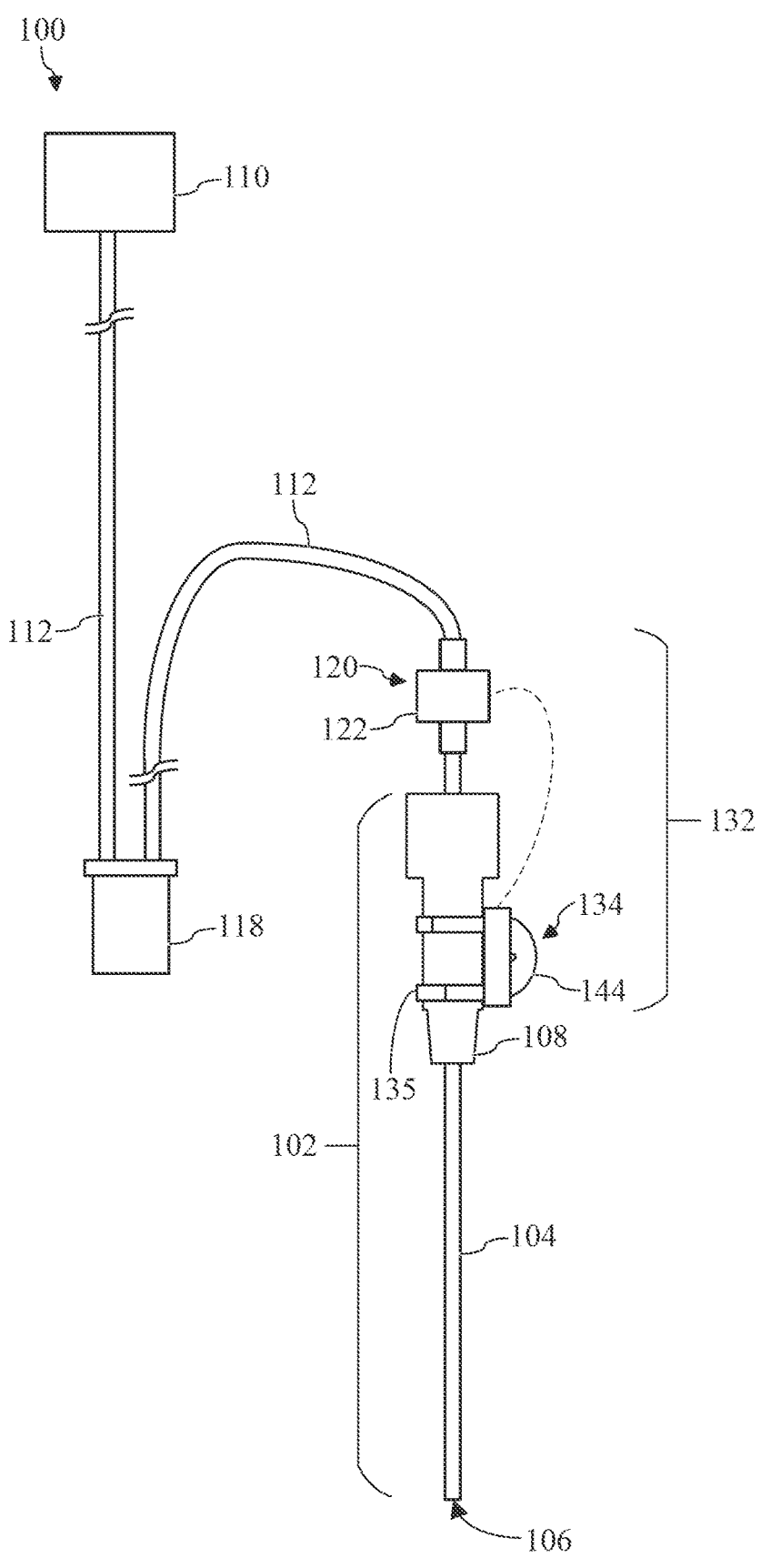
FIGS. 12A and 12B depict side views of endoscope system embodiments of the present disclosure.
Figure 12B:
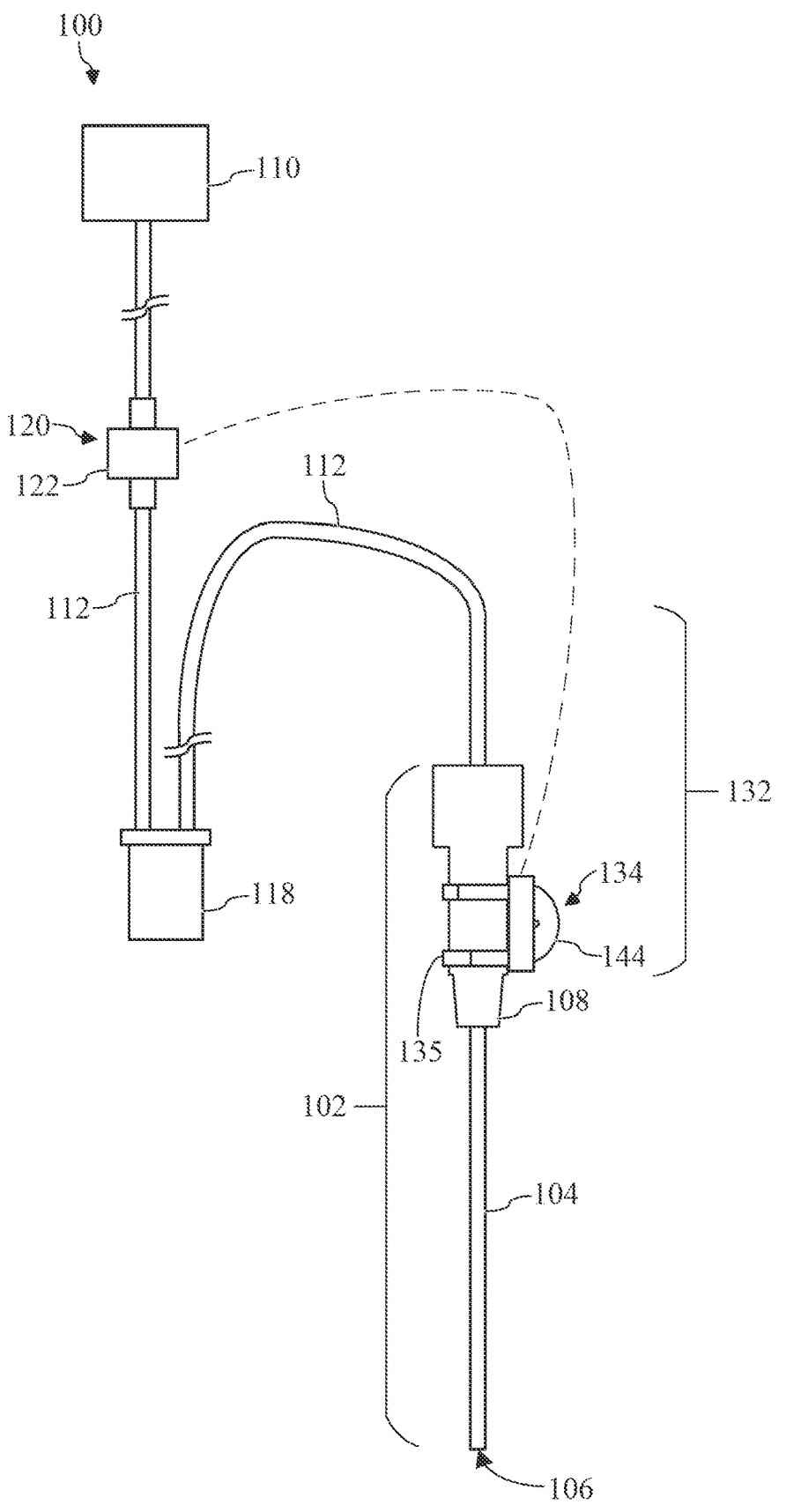

In FIGS. 12A and 12B, control device 134 may be formed as a dial switch 144. Dial switch 144 may be rotated by a user of endoscope 102 during the procedure to adjust/control the suction force provided to endoscope 102. Similar to toggle switch 140, push button switch 142/dial switch 144 may be electrically coupled to and/or in electronic communication with suction regulator device 122. As shown in FIG. 12A, in embodiments, suction regulator device 122 is positioned upstream from specimen container 118 and downstream from handpiece 108. As shown in FIG. 12B, in embodiments, suction regulator device 122 is positioned downstream from specimen container 118.

Figure 13A:
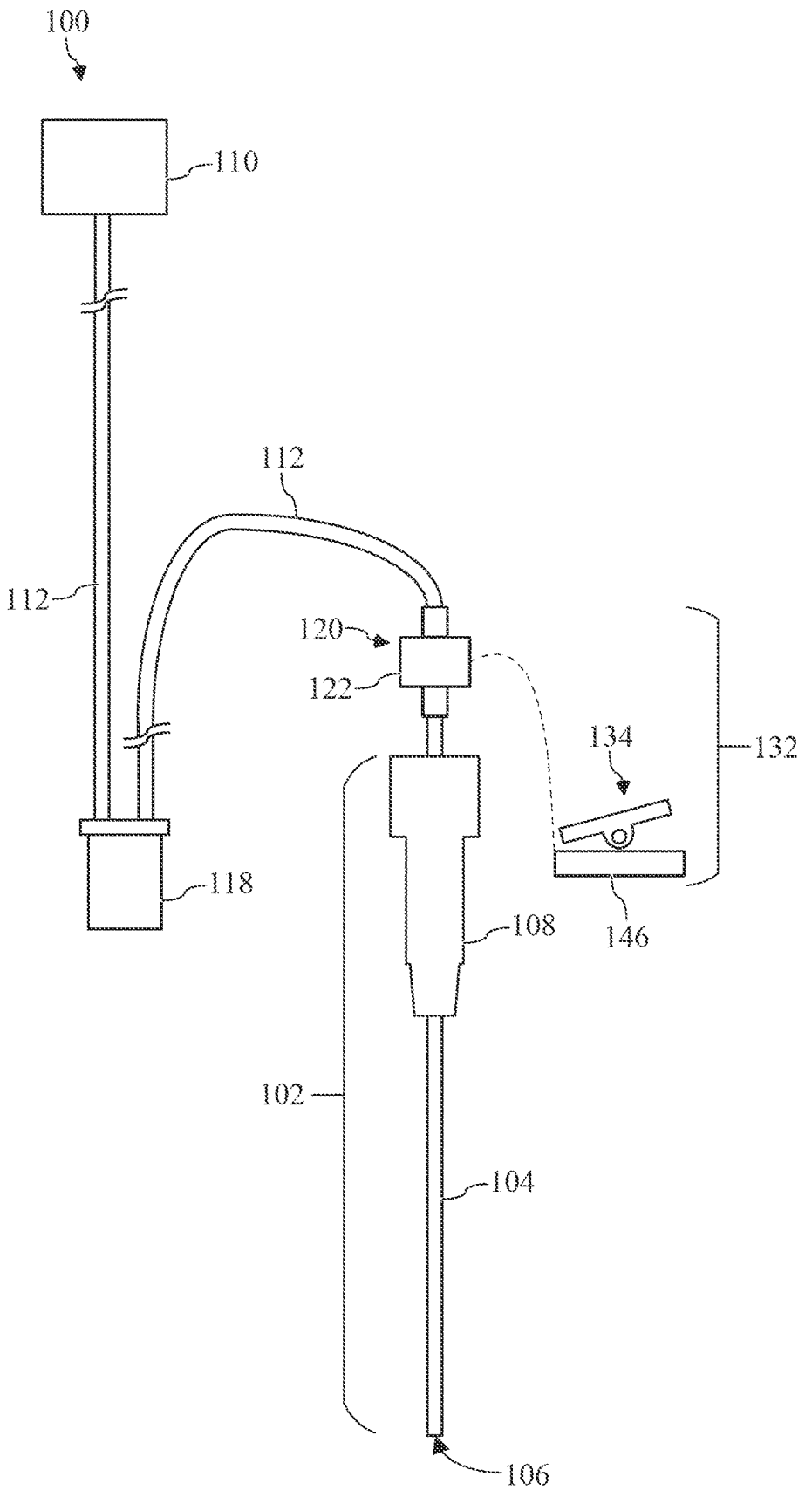
FIGS. 13A and 13B depict side views of endoscope system embodiments of the present disclosure.
Figure 13B:
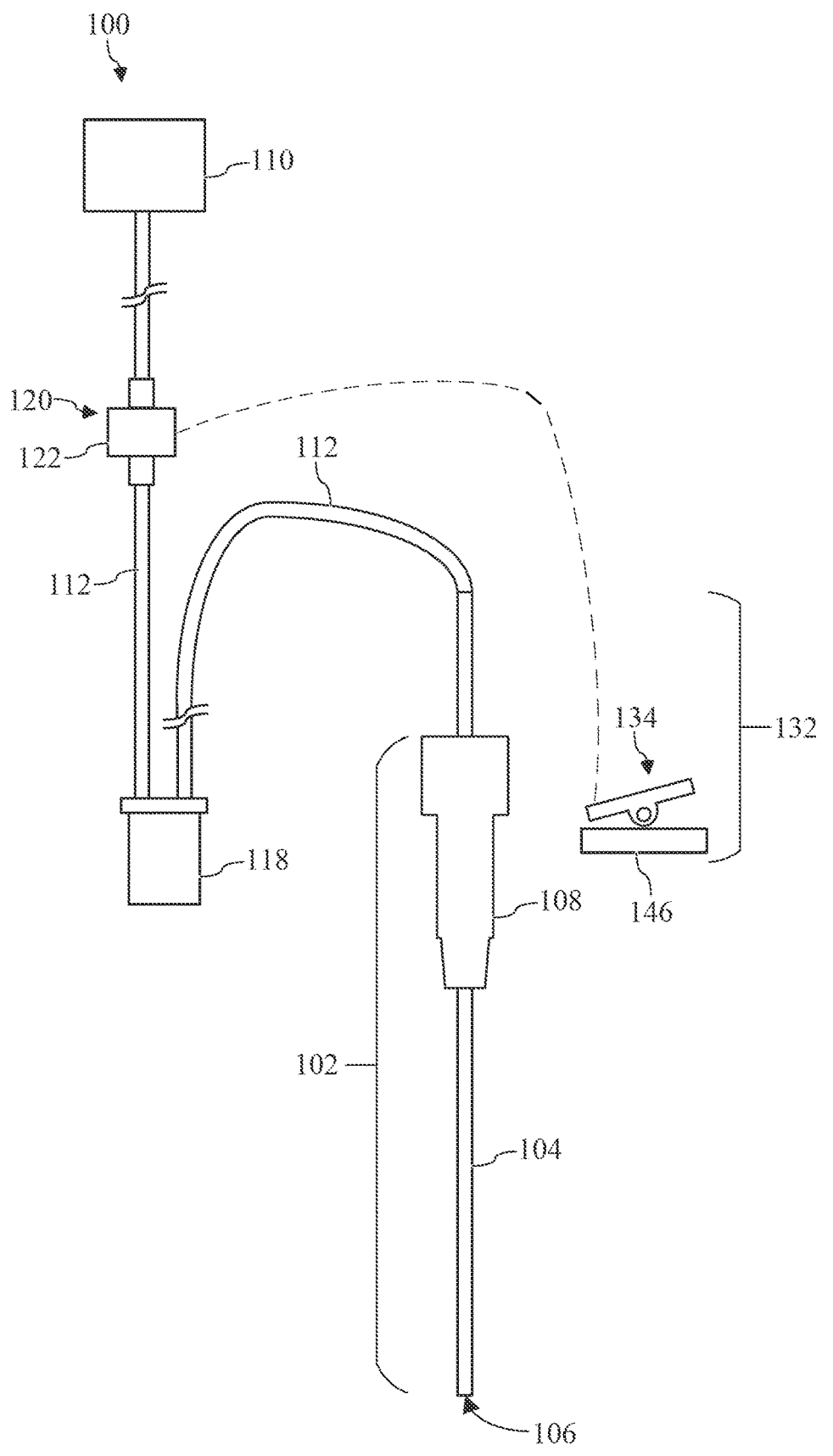

FIGS. 13A and 13B show additional non-limiting examples of a portable suction system 132. As shown, control device 134 may not be releasably coupled to handpiece 108 of endoscope 102. Rather, control device 134 may be a stand-alone device that is in electronic communication with and/or electrically coupled to suction regulator device 122. In the non-limiting example shown in FIGS. 13A and 13B, control device 134 of portable suction system 132 may be formed as an adjustable (foot) pedal 146. During the procedure, the user may maneuver endoscope 102 using both hands, and may simultaneously control/adjust the suction force provided by suction source 110 using adjustable pedal 146. As shown in FIG. 13A, in embodiments, suction regulator device 122 is positioned upstream from specimen container 118 and downstream from handpiece 108. As shown in FIG. 13B, in embodiments, suction regulator device 122 is positioned downstream from specimen container 118.

Although shown herein, in embodiments, as being positioned between endoscope 102 and specimen container 118, it is understood that suction regulator device 122 of portable suction system 132 may be positioned within endoscope system 100 in any location discussed herein. Additionally, one suction regulator device 122 is shown in each of the non-limiting examples of endoscope system 100. It is understood that the number of suction regulator devices included in endoscope system 100 is illustrative, and as such endoscope system 100 and/or portable suction system 132 may include more suction regulator devices 122 then shown herein.

Figure 14:
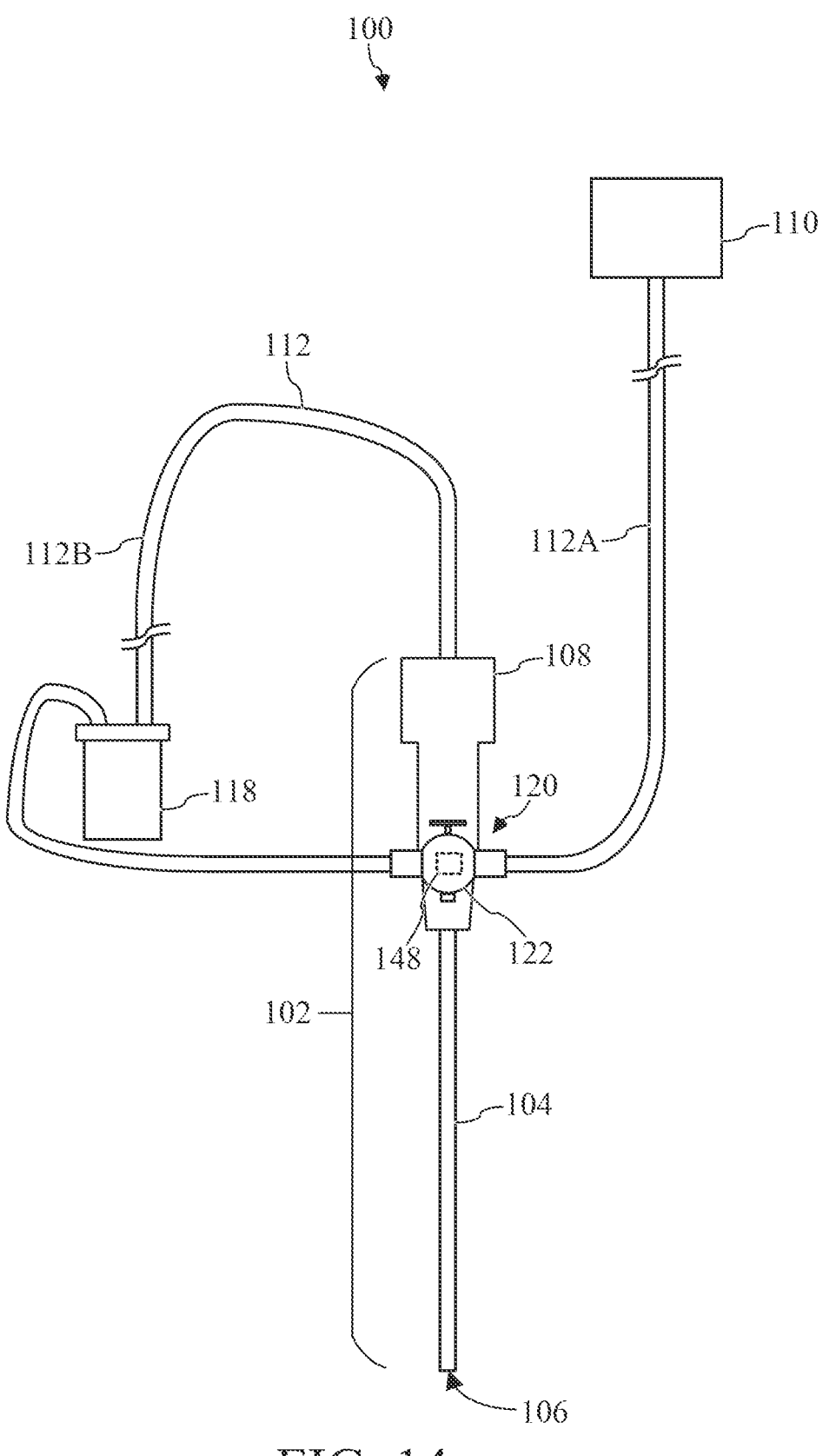
FIG. 14 shows a side view of an endoscope system including an endoscope and suction regulator device, according to additional embodiments of this disclosure.
Figure 15:
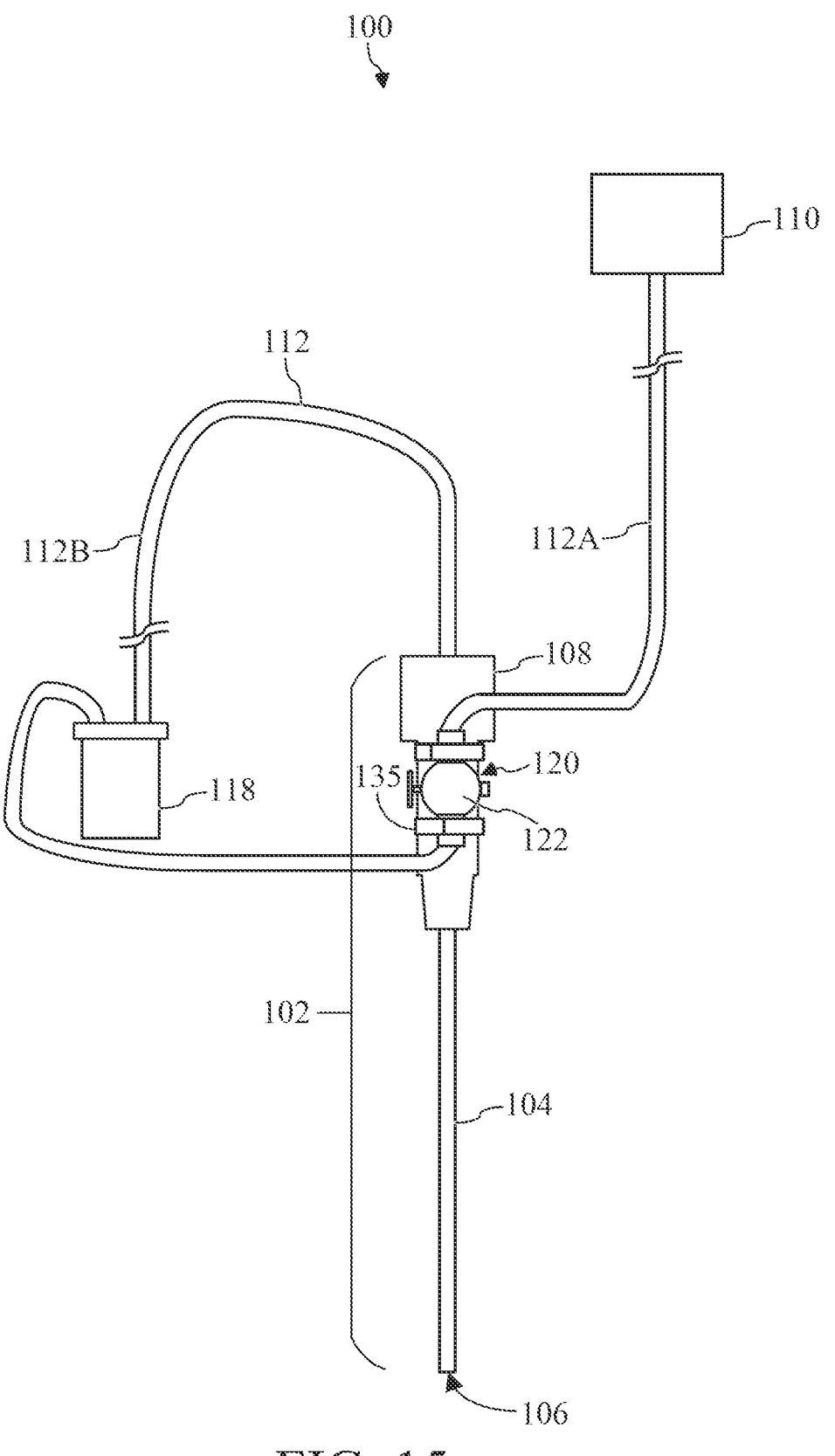
FIG. 15 shows a side view of an endoscope system including an endoscope and suction regulator device, according to further embodiments of this disclosure.

FIGS. 14 and 15 show additional non-limiting examples of endoscope system 100 including suction regulator devices 122. In the non-limiting examples, suction regulator devices 122 may be releasably coupled endoscope 102 of endoscope system 100. More specifically, suction regulator devices 122 may be releasably coupled, connected, and/or may contact handpiece 108 of endoscope 102. As similarly discussed herein, coupling suction regulator device 122 to handpiece 108 of endoscope 102 may all a user of endoscope system 100 (e.g., surgeon) to simultaneously perform the procedure using endoscope 102 and control/adjust the suction force provided by suction source 110 during the procedure using suction regulator device 122.

In the non-limiting example shown in FIG. 14, suction regulator device 122 may be releasably coupled, positioned on, and/or contact handpiece 108 of endoscope 102 via a connector component 148. That is, connector component 148 may extend from handpiece 108 and may releasably couple and/or connect suction regulator device 122 to handpiece 108. In this example, connector component 148 may also be positioned between handpiece 108 and suction regulator device 122.

In the non-limiting example shown in FIG. 15, suction regulator device 122 may be releasably coupled directly to, positioned directly on, and/or directly contact handpiece 108 of endoscope 102 via straps 135. That is, and as similarly discussed herein with respect to FIG. 9, straps 135 (e.g., hook-and-loop fasteners) may releasably coupled suction regulator device 122 and/or a portion of first suction tube 112A directly to handpiece 108 of endoscope 102. Additionally, straps 135 may allow for adjustment of the position of suction regulator device 122 releasably coupled to and/or positioned on handpiece 108 of endoscope 102.

FIG. 16 depicts example processes for performing an endoscopic procedure using an endoscope system including an endoscope and suction regulator devices/portable suction systems. In some cases, the procedure may be performed using endoscope system 100, endoscope 102, suction regulator devices 122, and/or portable suction systems 132, as discussed above with respect to FIGS. 1-15.

In process P1, a suction regulator device may be provided. The suction regulator device may be releasably coupled to and may be in communication with at least one suction tube of an endoscope system. The at least one suction tube may be in fluid communication with an endoscope of the endoscope system and a suction source of the endoscope system.

In process P2, the suction regulator device may be actuated. The suction regulator device may be actuated to at least one of increase or decrease a suction force within the at least one suction tube of the endoscope system. The suction regulator device may be continuously actuated to continuously increase or decrease a suction force.

As discussed herein, suction regulator devices 122 and/or portable suction systems 132 may be readily portable. As such, suction regulator devices 122 and/or portable suction systems 132 may be incorporated in and/or utilized by various endoscope systems or devices. Furthermore, suction regulator devices 122 and/or portable suction systems 132 may be integrated with any current endoscope system without the need for major redesign and/or additional, unconventional components. Rather, suction regulator devices 122 and/or portable suction systems 132 may simply be implemented within any endoscope system using no additional components, or alternatively simple suction tube splicing.

In some embodiments, the present disclosure includes a method of treating a patient in need thereof by contacting the patient with an endoscope system of the present disclosure. In embodiments, the contacting is for an effective duration to treat a patient. In embodiments, the treatment method includes actuating the suction regulator device to at least one of increase or decrease a suction force within the at least one suction tube of an endoscope system embodiment of the present disclosure. In embodiments, the procedure removes debris such as stones from a patient.

In embodiments, the present disclosure includes a suction device such as a portable suction device in fluid communication with an endoscope system, the suction device such as a portable suction device including: a suction regulator device releasably coupled to and in communication with at least one suction tube of the endoscope system, the at least one suction tube in fluid communication with an endoscope of the endoscope system and a suction source of the endoscope system, wherein the suction regulator device is actuatable to at least one of increase or decrease a suction force within the at least one suction tube. In embodiments, the suction regulator device includes one of an adjustable valve or an clamping component. In embodiments, the suction regulator device is positioned between the suction source and a specimen container, the specimen container positioned between and in fluid communication with the endoscope and the suction source. In embodiments, the suction regulator device is in direct fluid communication with: 1) a first suction tube, the first suction tube in direct fluid communication with the suction source, and 2) a second suction tube, the second suction tube in direct fluid communication with the specimen container. In embodiments, the suction regulator device is in communication with a suction tube in direct fluid communication with the suction source and the specimen container. In embodiments, the suction regulator device is positioned between and in direct fluid communication with: the specimen container, and a suction tube in direct fluid communication with the suction source. In embodiments, the suction regulator device is positioned between and in direct fluid communication with: the suction source, and a suction tube in direct fluid communication with the specimen container. In embodiments, the suction regulator device is positioned between the endoscope and a specimen container, the specimen container positioned between and in fluid communication with the endoscope and the suction source. In embodiments, the suction regulator device is in direct fluid communication with: a first suction tube, the first suction tube in direct fluid communication with the endoscope, and a second suction tube, the second suction tube in direct fluid communication with the specimen container. In embodiments, the suction regulator device is in communication with a suction tube in direct fluid communication with the endoscope and the specimen container. In embodiments, the suction regulator device is positioned between and in direct fluid communication with: the endoscope, and a suction tube in direct fluid communication with the specimen container. In embodiments, the suction regulator device is positioned between and in direct fluid communication with: the specimen container, and a suction tube in direct fluid communication with the endoscope.

In embodiments, the present disclosure includes a suction system such as a portable suction system, including: a suction regulator device releasably coupled to and in communication with at least one suction tube of an endoscope system, the at least one suction tube in fluid communication with an endoscope of the endoscope system and a suction source of the endoscope system; and a control device in communication with the suction regulator device, the control device actuating the suction regulator device to at least one of increase or decrease a suction force within the at least one suction tube of the endoscope system. In embodiments, the suction regulator device includes one of an adjustable valve or an clamping component. In embodiments, the control device is releasably coupled to a handpiece of the endoscope. In embodiments, the control device includes one of a: a variable trigger component, a toggle switch, a push button switch, or a dial switch. In embodiments, the control device includes an adjustable pedal. In embodiments, the control device is electrically coupled to the suction regulator device. In embodiments, the control device is coupled to and in communication with the suction regulator device via a tension cable. In embodiments, the suction regulator device is one of a motorized device or a manual device.

In embodiments, the present disclosure includes a method of performing a endoscopic procedure, the method including: providing a suction regulator device releasably coupled to and in communication with at least one suction tube of an endoscope system, the at least one suction tube in fluid communication with an endoscope of the endoscope system and a suction source of the endoscope system; and actuating the suction regulator device to at least one of increase or decrease a suction force within the at least one suction tube of the endoscope system.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/–10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A portable suction device in fluid communication with an endoscope system, the portable suction device comprising:

a suction regulator device in communication with at least one suction tube of the endoscope system, the at least one suction tube in fluid communication with an endoscope of the endoscope system and a suction source of the endoscope system, wherein the suction regulator is positioned directly adjacent to and directly coupled to a specimen container positioned between and in fluid communication with the endoscope and the suction source, and wherein the suction regulator device is actuatable to at least one of increase or decrease a suction force within the at least one suction tube.

2. The portable suction device of claim 1, wherein the suction regulator device includes one of an adjustable valve or a clamping component.

3. The portable suction device of claim 1, wherein the suction regulator device is positioned between the suction source and the specimen container.

4. The portable suction device of claim 1, wherein the suction regulator device is in communication with a suction tube in direct fluid communication with the suction source.

5. The portable suction device of claim 4, wherein the suction regulator device is positioned between and in direct fluid communication with:

the specimen container, and the suction tube in direct fluid communication with the suction source.

6. The portable suction device of claim 1, wherein the suction regulator device is positioned between the endoscope and the specimen container.

7. The portable suction device of claim 1, wherein the suction regulator device is in communication with a suction tube in direct fluid communication with the endoscope.

8. The portable suction device of claim 7, wherein the suction regulator device is positioned between and in direct fluid communication with:

the specimen container, and the suction tube in direct fluid communication with the endoscope.

* * * * *